United States Patent [19]

Zandbergen et al.

[11] Patent Number: 5,563,412
[45] Date of Patent: Oct. 8, 1996

[54] METHOD OF MAKING SPECIMENS FOR AN ELECTRON MICROSCOPE

[75] Inventors: Hendrik W. Zandbergen, Katwijk; Anthonius Van Veen, Bergschenhoek, both of Netherlands

[73] Assignee: U.S. Philips Corporation, New York, N.Y.

[21] Appl. No.: 328,228

[22] Filed: Oct. 25, 1994

[30] Foreign Application Priority Data

Oct. 28, 1993 [BE] Belgium ................ 09301154

[51] Int. Cl.⁶ ........................... H01J 37/26
[52] U.S. Cl. ............... 250/307; 250/306; 250/311; 204/192.32
[58] Field of Search ............... 250/307, 306, 250/310, 311, 492.2, 492.21, 492.3; 204/192.32, 192.38, 298.31, 298.32; 156/643.1, 345 P; 216/67

[56] References Cited

U.S. PATENT DOCUMENTS

| 4,492,610 | 1/1985 | Okano et al. | 156/643 |
| 5,241,186 | 8/1993 | Yunogami et al. | 250/307 |
| 5,328,515 | 7/1994 | Chouan et al. | 156/345 |
| 5,440,123 | 8/1995 | Ikeda | 250/307 |

FOREIGN PATENT DOCUMENTS

| 1780127 | 12/1992 | European Pat. Off. |
| 684493 | 3/1994 | Japan ............... 250/306 |

OTHER PUBLICATIONS

J. D. Chinn, "Magnetro–plasma ion beam etching: A new dry etching technique", J. Vac. Sci. Tech., May/Jun. 1988, pp. 1379–1383.

*Primary Examiner*—Jack I. Berman
*Assistant Examiner*—Kiet T. Nguyen
*Attorney, Agent, or Firm*—Leroy Eason

[57] ABSTRACT

A method and device for preparing a specimen of material for examination by a particle-optical microscope apparatus such as a high-resolution electron microscope (HREM). The known ion milling technique enables specimens to be made sufficiently thin so as to be electron-transparent, that being a condition for HREM materials examination. However, that results in amorphous material on the surface of the specimen which may cause blurring of the image of the surface and also lead to incorrect materials analysis. In accordance with the invention, the surface of the specimen is subjected, possibly following ion milling, to ion bombardment from a plasma of ionized gas which is formed adjoining such surface. This achieves ion etching of the surface, and consequent reduction of the thickness of the specimen, without formation of disturbing amorphous regions on the surface.

8 Claims, 3 Drawing Sheets

METHOD OF MAKING SPECIMENS FOR AN ELECTRON MICROSCOPE

BACKGROUND OF THE INVENTION

1. Field of the Invention

The invention relates to a method of making specimens for examination by means of a particle-optical microscope apparatus.

The invention also relates to a device for carrying out the method and to a particle-optical microscope apparatus comprising such a device.

2. Related Art

Many materials of interest nowadays from the point of view of materials science have properties which are determined by their microstructure; examples in this respect are materials with crystallites of dimensions in the nanometer range, multilayer structures such as used for X-ray reflection, and microelectronic components. In order to understand their macroscopic properties, it is of essential importance to determine the structure properties at an atomic scale. Also examinations at a molecular scale are important not only for materials science also for biological specimens as well.

The properties at such a small scale can be determined by means of a particle-optical microscope apparatus such as an electron microscope. Therefore, it is necessary to make specimens for examination in such apparatus from which the desired material properties can be determined. Such specimens should preferably be so thin that they are transparent to electrons of an energy which is customary in electron microscopes.

For electron microscopy there are a number of methods of making electron-transparent specimens which are known, for example pulverizing, ultramicrotomy, chemical polishing and ion milling. Each of these methods, however, has its own drawbacks, which make the relevant method unattractive or even completely unsuitable for making specimens for the purpose of materials examination at an atomic scale.

Upon pulverization of multi-component systems (such as, for example an integrated semiconductor in which metal connections are attached to semiconductor material), the boundaries between the components are usually lost. Particularly these boundaries are of interest to materials science, so that specimens made according to this method can be used to a limited extent only. Ultramicrotomy is a method of making slices of specimens with a thickness of more than 5 nm. This method, however, cannot be used very well in the case of hard materials because the large forces occurring during cutting cause many faults (such as dislocations and fractures) in the material to be studied, so that an incorrect impression of the structure of the material is obtained. For chemical polishing a liquid with a solvent is conducted across the specimen material (for example, acid across metal). If the specimen is thin enough, the supply of liquid is terminated. After this treatment, however, a surface layer remains which has a structure and/or composition which deviates from those of the original material. The structure which remains often has the appearance of an amorphous layer. Ion milling is a technique for the formation of specimens by subjecting a thin slice of the specimen material to a surface treatment by charged particles, so that surface layers of the slice of the specimen material are removed. The charged particles (ions) are applied to the specimen with an acceleration voltage of a few kilovolts at a small angle (for example, 10°) relative to the specimen surface. This technique enables the manufacture of specimens which are sufficiently thin for the described materials examination. However, this method of surface treatment also appears to leave an amorphous layer behind on the specimen surface.

An amorphous layer on the surface of a specimen, or an amorphous region which partly covers the surface, seriously hampers the described examination. An amorphous layer which completely covers the specimen leads to blurting of the image of the specimen; moreover, the chemical analysis of the surface thus becomes less reliable. It has been found that a partly covering amorphous layer acts as a kernel for the growth of a fully amorphous layer when the specimen is exposed to an electron beam, so that the already described problems relating to a completely amorphous surface occur.

SUMMARY OF THE INVENTION

It is an object of the invention to provide a method of making specimens for examination by means of a particle-optical apparatus which enables specimens to be made which are sufficiently thin and which exhibit a surface structure which has not been influenced in a disturbing manner by the method used to make the specimen thinner.

To this end, the method of the invention is characterized in that the surface treatment includes bringing a specimen surface into contact with ions extracted from a neighbouring plasma.

Experiments and computer simulations have demonstrated that the plasma treatment in accordance with the invention does not cause a disturbing amorphisation of the surface. Moreover, no amorphous regions are formed of a dimension such that they can act as a kernel for further amorphisation by the electron beam. An additional advantage of the method of the invention consists in that adsorbed hydrocarbons contaminating the specimen can also be removed. Such contamination is caused, for example by hydrocarbons (oil) from the vacuum pump which penetrate the vacuum space and adhere to the specimen surface. This oil is decomposed by the electron beam, thus causing hydrocarbon contamination of the specimen. It has been found that these hydrocarbons are removed by the proposed method. In a specimen thus treated it is very well possible, after selection of a region to be analysed, to carry out the analysis while at the same time observing the relevant region without giving rise to masking by carbon contamination.

It is advantageous that the process can be controlled in dependence on a variety of circumstances, such as the nature of the material to be examined. To this end, the method of the invention is characterized in that there is applied an electric field in which the plasma and the specimen surface to be treated are both situated. The electric field enables adjustment of the optimum distance between the plasma and the specimen (in an energy-dependent manner) and also control of the direction of incidence and the energy of the charged particles in the plasma as desired; the process can thus be optimized in dependence on, for example the material to be examined. The electric field may then extend substantially perpendicularly to the specimen surface to be treated.

In given circumstances it may occur that the material removed by the plasma on one side of the specimen is deposited again on its other side. This risk exists notably when a hole is etched into the specimen and the edges of the hole are sharp and hence form a very thin electron-transparent region. The material removed at the upper side of the hole edges could then be deposited again in amorphous form on the lower side. In order to counteract this effect, the invention is also characterized in that the surface treatment is performed on two oppositely situated sides of the specimen.

After treatment by the plasma, the specimen is positioned in a particle-optical apparatus so as to be studied. In dependence on the specimen material, protective steps must be taken to prevent oxidation by ambient air or other contaminations. This is substantially simplified when the method of the invention is carried out in an evacuated space which is in vacuum contact with the examination space of the particle-optical apparatus (the electron microscope). More specifically, the space for plasma treatment may directly adjoin the specimen space of the electron microscope, or the treatment can even be performed in this space. The electron microscope is then rendered suitable for carrying out the method of the invention by installation of a device in accordance with the invention.

A device for carrying out the method in accordance with the invention is characterized in that at least the outer surface of the specimen holder is made of an electrically insulating material in the vicinity of the specimen location. This material may be, for example aluminium oxide. It is thus achieved that the specimen holder itself is not exposed to the etching effect of the ions from the plasma. As a result, the specimen holder will not be damaged and, moreover, no contaminating etching products from the specimen holder will be introduced into the plasma space.

BRIEF DESCRIPTION OF THE DRAWINGS

The invention will be described in detail hereinafter with reference to the Figures in which corresponding elements are denoted by corresponding reference numerals.

Therein.

DESCRIPTION OF THE PREFERRED EMBODIMENTS

Figure 1:
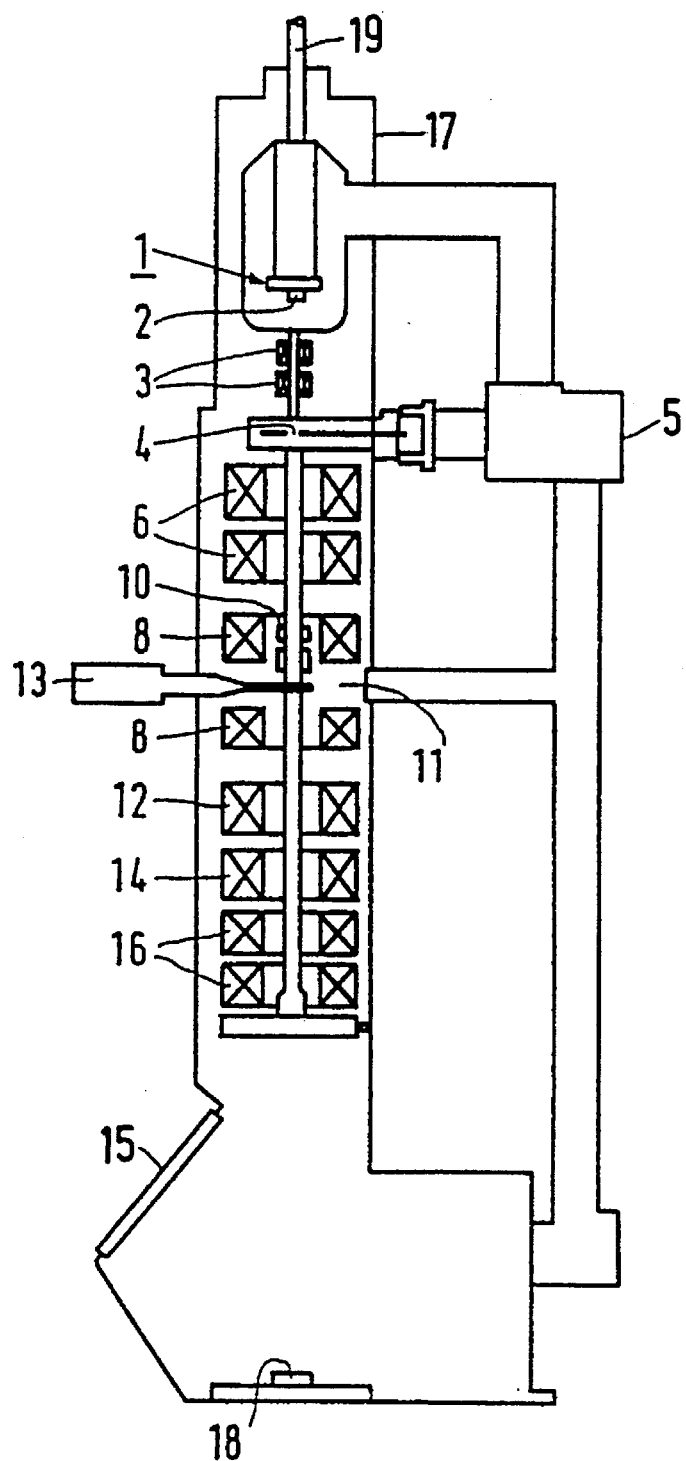
FIG. 1 shows an electron microscope comprising a device for carrying out the method of the invention.

The electron microscope shown in FIG. 1 comprises an electron source 1 with an electron-emissive element 2, a beam alignment system 3, a beam diaphragm 4, a condensor lens 6, an objective lens 8, a beam scanning system 10, an object space 11 in which a specimen carrier 13 is accommodated, a diffraction lens 12, an intermediate lens 14, a projection lens 16 and an electron detector 18. The objective lens 8, the intermediate lens 14 and the projection lens 16 together constitute an imaging lens system. These elements are accommodated in a housing 17 with an electrical supply lead 19 for the electron source, a viewing window 15 and a vacuum pumping device 5. The specimen carder 13 may be combined with a loading unit (not shown in this Figure) for loading the specimens into the object space 11; this loading unit will be described with reference to FIG. 4. The microscope may also comprise a device for plasma etching which is not shown either in this Figure; this device will be described with reference to the FIGS. 3 and 4.

Figure 2:
FIG. 2 shows diagrammatically a specimen for observation in an electron microscope.

FIG. 2 is a diagrammatic representation of the cross-section of a specimen which consists of a region 21 of a crystalline material on which a layer 22 of an amorphous material is present. This specimen is obtained, for example by ion milling of a thin slice of a specimen material, the ions having acted on the material inter alia at the area of the opening 24 produced by this effect. However, it is alternatively possible to prepare the specimen in another way, for example by means of said chemical polishing method. Thus, a wedge-shaped part is obtained which, at the area of the end 23, is sufficiently thin for examination by high-resolution electron microscopy. Even though ion milling thus enables formation of a specimen which is sufficiently thin, the problem of the amorphous layer on the specimen continues to exist. The treatment involving plasma etching offers a solution in this respect.

Figure 3:
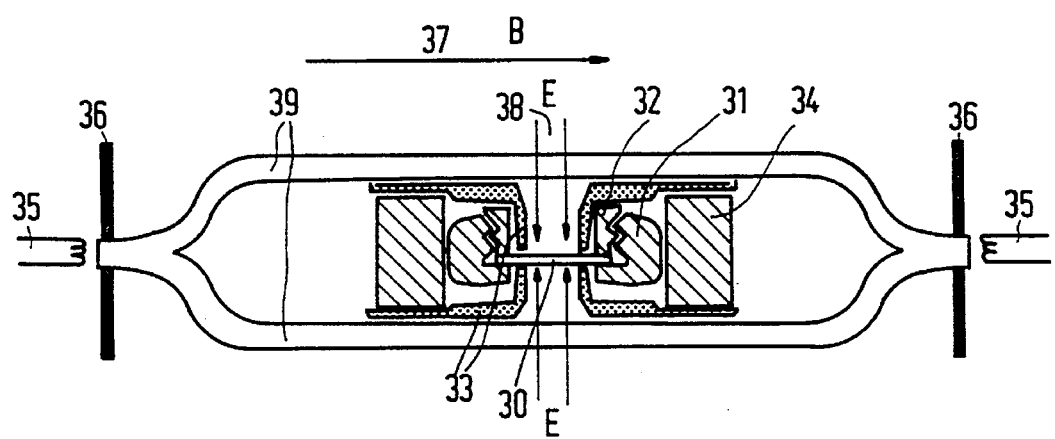
FIG. 3 shows diagrammatically the construction of a device for carrying out the method of the invention.

FIG. 3 is a sectional view of a device for plasma treatment in accordance with the invention. The specimen 30 is accommodated in a metal holder 31 in which it is secured by a ring 32 screwed into the holder 31. The specimen holder 31 is present in an electrically insulating holder 34. Underneath and above the specimen 30 there is provided an electrically insulating shroud 33 which prevents the metal holder 31, 32 from being exposed to plasma ions. The plasma is generated by means of electrons produced by filaments 35. The electrons are aligned and accelerated by diaphragms 36 which can receive a voltage other than that of the filaments for this purpose. Between the two diaphragms there is applied a magnetic field B, represented by the arrow 37, for example by means of coils which are not shown in the Figure. Also present is an electric field E which is produced by electrodes which are not shown in the Figure; this field is represented by arrows 38. A gas to be ionized is present in the space between the diaphragms 36. The choice of this gas is dependent on the material to be treated. For example, iodine can be chosen for the treatment of gallium arsenide (GaAs). For other purposes a noble gas will be chosen; experiments have shown that argon is a suitable plasma gas. Argon is ionized by the electrons emanating from the filaments 35. The electrons and the plasma ions are prevented from spreading across the entire space by the magnetic field 37. A ribbon-like plasma 39 is thus obtained to both sides of the specimen. By applying a voltage which deviates from the environment to the specimen, an electric field extending approximately perpendicularly to the specimen is obtained. Ions are thus driven from the plasma in the direction of the specimen so as to realise the etching effect. Experiments have demonstrated that a suitable etching effect is obtained with a voltage of the order of magnitude of from 30 eV to 200 eV.

Figure 4A:
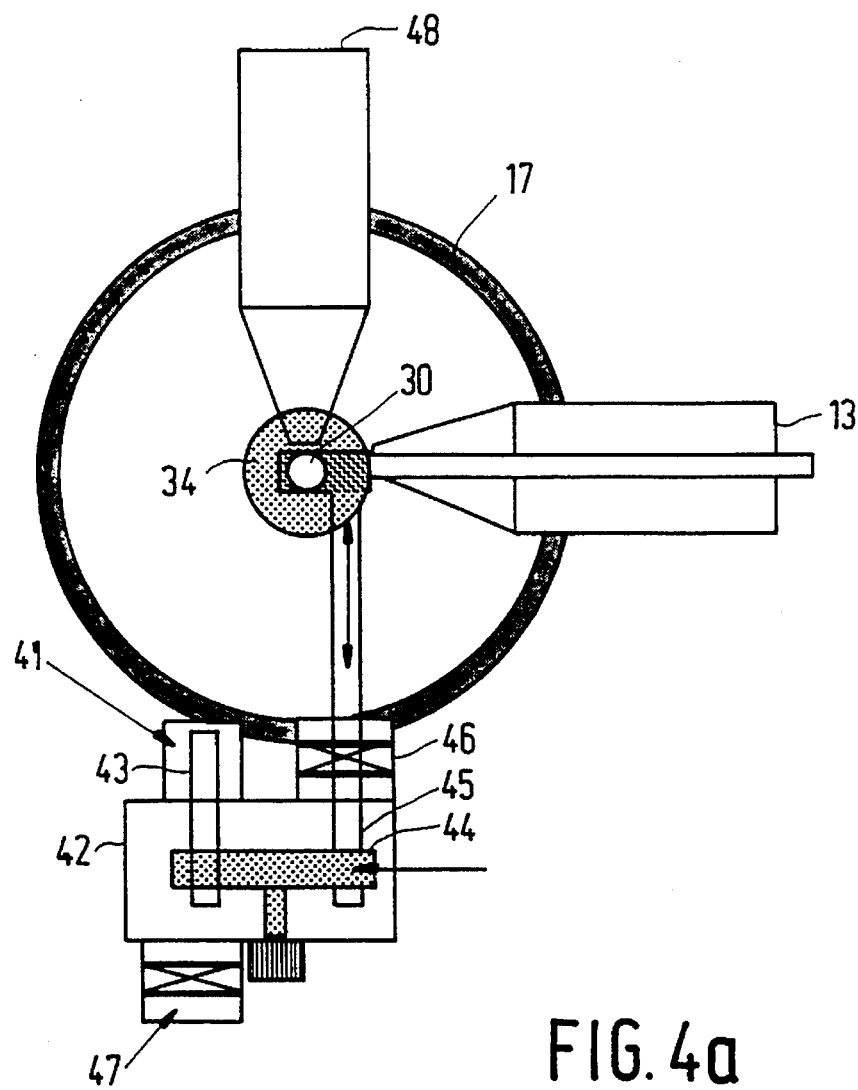
FIG. 4(a–b) shows a unit for loading and unloading specimens treated in conformity with the method of the invention into and from an electron microscope, FIG. 4a being a plan view and FIG. 4b a front view.
Figure 4B:
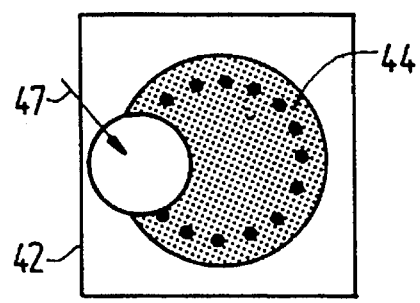

FIG. 4a is a cross-sectional view of the column of an electron microscope in which the device for plasma etching is accommodated, FIG. 4b being a front view of the loading and unloading device 42. The housing 17 of the microscope accommodates a specimen carrier 13 on which a holder 34 for the specimen 30 is secured. The housing 17 is provided with a loading and unloading unit 42 which comprises a plasma device 41 in accordance with the invention. Specimens to be treated are introduced into the loading and unloading unit 42 by means of a transporter 43, via a lock 47. The specimen is thus transported to the plasma device 41 for plasma treatment. Subsequent to this treatment, the specimen is displaced, via a carrousel 44, to a transporter 45 which transfers the specimen to the specimen carder 34 via a lock 46. The entire treatment of the specimen can thus take place in vacuum.

We claim:

1. A method of preparing a specimen of material for examination by a particle-optical microscope apparatus, comprising the steps of:

deriving a thin slice of the specimen;

forming a plasma of ionized gas adjoining at least one surface of the slice; and applying an electric field across the plasma and the slice to extract ions from the plasma which impact upon and thereby etch said surface of the slice, the electric field extending substantially perpendicular to said surface and having a field strength such that the energy of the ions from the plasma is between 30 eV and 200 eV;

the ion etching of said surface of the slice reducing the thickness of the slice without significant amorphization of said surface.

2. A method as claimed in claim 1, wherein the slice has a first and a second surface, said plasma has a first branch adjoining said first surface of the slice and a second branch adjoining said second surface of the slice, and each of said surfaces is subjected to ion etching by ions extracted from the adjoining branch of said plasma.

3. A method as claimed in claim 1, performed within an evacuated space which is in vacuum contact with the examination space of the particle-optical microscope apparatus.

4. A device for preparing a specimen of material for examination by a particle-optical microscope apparatus, comprising:

a holder having a location therein for supporting a thin slice of the specimen while leaving at least one surface of said slice exposed;

means for forming a plasma of ionized gas adjoining said one surface of said slice; and means for establishing an electric field across the plasma and the slice which extracts ions from said plasma which impact upon and thereby etch said one surface of the slice, the electric field extending substantially perpendicular to said one surface and having a field strength such that the energy of the ions from the plasma is between 30 eV and 200 eV;

whereby the ion etching of said one surface of the slice causes reduction of the thickness of the slice without significant amorphization of said one surface.

5. A device as claimed in claim 4, wherein said holder supports said slice with both surfaces thereof exposed, said plasma is formed with a first branch adjoining said one surface of said slice and a second branch adjoining the other surface of said slice, and said electric field extracts ions from both branches of said plasma which impact upon and thereby etch both surfaces of said slice.

6. A device as claimed in claim 4, wherein said plasma is in the form of at least one ribbon of ionized gas which adjoins said one surface of said slice at some distance therefrom.

7. A device as claimed in claim 4, wherein said holder has an outer surface which, at least in the vicinity of the supporting location therein for said slice, is made of electrically insulating material.

8. A device as claimed in claim 4, comprised in a vacuum space which is in vacuum contact with the examination space of said particle-optical apparatus.

* * * * *